US012575686B2

(12) United States Patent
Moore et al.

(10) Patent No.: US 12,575,686 B2
(45) Date of Patent: Mar. 17, 2026

(54) DISPOSABLE CHANGING ARTICLE SYSTEMS AND METHODS

(71) Applicant: POTTY PAD WITH POCKETS, LLC, Albuquerque, NM (US)

(72) Inventors: Antoinette V. Moore, Albuquerque, NM (US); Jarrod M. Moore, Albuquerque, NM (US); Theresa A. Walton, Albuquerque, NM (US)

(73) Assignee: POTTY PAD WITH POCKETS, LLC, Albuquerque, NM (US)

( * ) Notice: Subject to any disclaimer, the term of this patent is extended or adjusted under 35 U.S.C. 154(b) by 311 days.

(21) Appl. No.: 17/811,367

(22) Filed: Jul. 8, 2022

(65) Prior Publication Data

US 2024/0008657 A1     Jan. 11, 2024

(51) Int. Cl.
*A47D 5/00* (2006.01)
*A61F 13/84* (2006.01)

(52) U.S. Cl.
CPC ................ *A47D 5/00* (2013.01); *A61F 13/84* (2013.01)

(58) Field of Classification Search
CPC ....... A61F 13/84; A61F 5/485; A47D 15/003; A47D 5/00; A01K 23/005
USPC .......................................... 5/484
See application file for complete search history.

(56) References Cited

U.S. PATENT DOCUMENTS 3,626,900 A * 12/1971 Failla ................... A01K 1/0107
                                                    119/161
4,702,378 A * 10/1987 Finkel ..................... A61F 15/00
                                                    206/581

4,939,017 A * 7/1990 Foxman .................. A61F 5/485
                                                    428/192
11,033,169 B1 * 6/2021 Rozner ................... A47L 13/16
2004/0261208 A1 * 12/2004 McKay ................. B32B 27/304
                                                    15/215
2007/0000446 A1 * 1/2007 Dunn ................... A01K 1/0107
                                                    119/161
2008/0229506 A1 * 9/2008 Saman .................. A47D 5/006
                                                    5/655

(Continued)

FOREIGN PATENT DOCUMENTS

DE      202020000651 U1 * 5/2020
WO      WO-03070123 A2 * 8/2003 ........... A47D 15/003
(Continued)

OTHER PUBLICATIONS

WO-2021210569-A1-Eng Translation (Year: 2021).*

(Continued)

*Primary Examiner* — Justin C Mikowski
*Assistant Examiner* — Amanda L Bailey
(74) *Attorney, Agent, or Firm* — Dorsey & Whitney LLP

(57)                    ABSTRACT

Disposable diaper changing article systems and methods are provided. A disposable changing article may include a body including a central portion and a perimeter edge surrounding the central portion. The disposable diaper changing article may include at least one storage pocket. Each storage pocket may be positioned at the perimeter edge and include an opening directed toward the central portion of the body. A system may include the disposable diaper changing article and a changing accessory for positioning within the at least one storage pocket. A method of manufacturing the disposable diaper changing article is also provided.

18 Claims, 3 Drawing Sheets

(56)                    References Cited

U.S. PATENT DOCUMENTS

2009/0152160  A1 *   6/2009  Thompson ............. A47D 5/006
                                                          206/581
2012/0311788  A1 *  12/2012  Jackson, II  ......... A47D 15/003
                                                            5/655
2022/0117426  A1 *   4/2022  Soleimani ............ A47G 27/025

FOREIGN PATENT DOCUMENTS

WO      WO-2005002385  A1 *   1/2005   ........... A45C 7/0095
WO      WO-2021210569  A1 *  10/2021

OTHER PUBLICATIONS

WO-03070123-A2-Eng Translation (Year: 2003).*
Nihao Honey Baby Disposable Changing Pad, 100 Count Inconti-
nence Changing Pad with Breathable, Waterproof, Soft Non-Woven
Fabric, and Leak Proof Quick Absorb (13×18in,Pink); retrieved
from the internet Oct. 3, 2022: https://www.amazon.com/dp/
B086SLN5CD/ref=sspa_dk_detail_2?th=1.

* cited by examiner

500

502

Define a body including an
absorbent pad and a
perimeter edge surrounding
the absorbent pad

504

Define at least one storage
pocket at the perimeter edge

506

Place at least one changing
accessory in the at least one
storage pocket

DISPOSABLE CHANGING ARTICLE SYSTEMS AND METHODS

TECHNICAL FIELD

One or more embodiments relate generally to disposable changing articles and, more particularly, to systems and methods for a disposable changing pad having one or more storage pockets configured to conveniently place one or more changing accessories.

BACKGROUND

Conventional systems and methods of changing diapers can be expensive and/or inconvenient. Changing diapers on-the-go can be especially inconvenient, particularly in locations or places without dedicated changing stations. Public changing stations can also be unsanitary and/or provide a limited changing area to place changing accessories (e.g., diaper, wipes, ointment, etc.) within arm's reach and/or in a convenient location.

Therefore, there is a need in the art for systems and methods that address the above deficiencies, other deficiencies known in the industry, or at least offers an alternative to current techniques.

SUMMARY

Systems and methods are provided for disposable changing articles. According to one or more embodiments of the present disclosure, a disposable changing article may include a body including a central portion and a perimeter edge surrounding the central portion. The disposable changing article may include at least one storage pocket. Each storage pocket may be positioned at the perimeter edge and include an opening directed toward the central portion of the body.

According to one or more embodiments of the present disclosure, a system is provided. The system may include a disposable changing article. The disposable changing article may include a body including an absorbent pad and a perimeter edge surrounding the absorbent pad. The disposable changing article may include at least one storage pocket, each storage pocket positioned at the perimeter edge and including an opening directed toward the absorbent pad. The system may include a changing accessory for positioning within the at least one storage pocket.

According to one or more embodiments of the present disclosure, a method of manufacturing a disposable changing article is provided. The method may include defining a body including an absorbent pad and a perimeter edge surrounding the absorbent pad. The method may further include defining at least one storage pocket at the perimeter edge. Each storage pocket may include an opening directed toward the absorbent pad of the body.

Additional features are set forth in part in the description that follows and will become apparent to those skilled in the art upon examination of the specification and drawings or may be learned by the practice of the disclosed subject matter. A further understanding of the nature and advantages of the present disclosure may be realized by reference to the remaining portions of the specification and the drawings, which forms a part of this disclosure.

One of skill in the art will understand that each of the various aspects and features of the disclosure may advantageously be used separately in some instances, or in combination with other aspects and features of the disclosure in other instances. Accordingly, individual aspects can be claimed separately or in combination with other aspects and features. Thus, the present disclosure is merely exemplary in nature and is in no way intended to limit the claimed invention or its applications or uses. It is to be understood that structural and/or logical changes may be made without departing from the spirit and scope of the present disclosure.

The present disclosure is set forth in various levels of detail and no limitation as to the scope of the claimed subject matter is intended by either the inclusion or non-inclusion of elements, components, or the like in this summary. In certain instances, details that are not necessary for an understanding of the disclosure or that render other details difficult to perceive may have been omitted. Moreover, for the purposes of clarity, detailed descriptions of certain features will not be discussed when they would be apparent to those with skill in the art so as not to obscure the description of the present disclosure. The claimed subject matter is not necessarily limited to the arrangements illustrated herein, with the scope of the present disclosure is defined only by the appended claims.

BRIEF DESCRIPTION OF THE DRAWINGS

The description will be more fully understood with reference to the following figures in which components may not be drawn to scale, which are presented as various embodiments of the measuring device described herein and should not be construed as a complete depiction of the scope of the measuring device and associated chainsaw system.

Embodiments of the disclosure and their advantages are best understood by referring to the detailed description that follows. It should be appreciated that like reference numerals may be used to identify like elements illustrated in one or more of the figures.

DETAILED DESCRIPTION

Figures 1, 2:
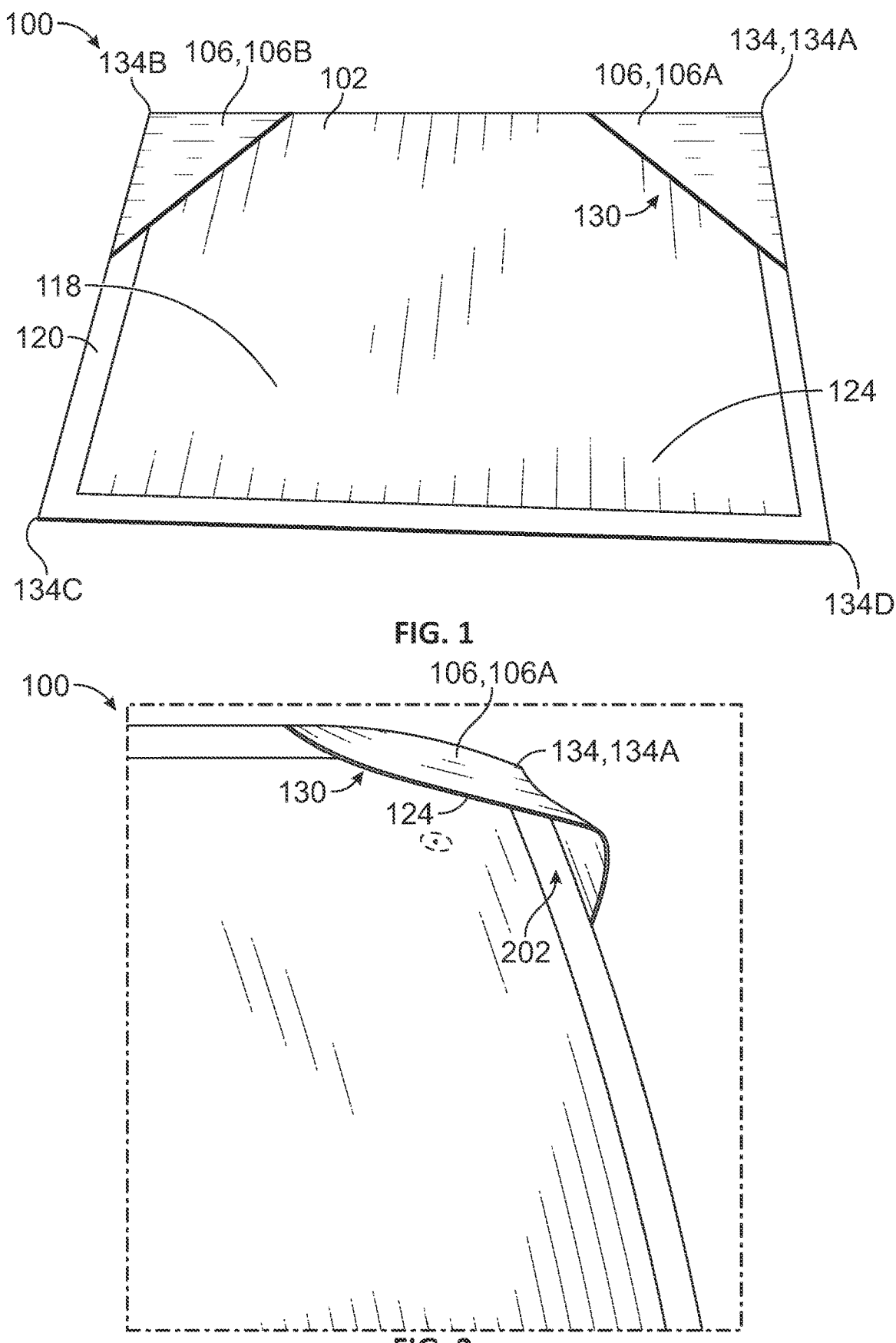
FIG. 1 illustrates a perspective view of a disposable changing article, in accordance with an embodiment of the disclosure.
FIG. 2 illustrates a fragmentary view of the disposable changing article and showing a corner of the disposable changing article, in accordance with an embodiment of the disclosure.

FIG. 1 illustrates a perspective view of a disposable changing article 100, in accordance with an embodiment of the disclosure. Referring to FIG. 1, disposable changing article 100, hereinafter referred to as "changing article" for convenience without intent to limit, may include a body 102 and at least one storage pocket 106 for storing one or more items. For example, one or more changing items or accessories 110, such as wipes, diapers, ointment (e.g., diaper rash cream, petroleum jelly, etc.), lotion, or other items/accessories (hereinafter referred to as "changing accessory" for convenience without intent to limit), may be placed in one or more storage pockets 106 for convenient location of the changing accessory 110 during diaper changing (see FIG. 3).

In embodiments, one or more storage pockets 106 may be used to hold used or soiled diapers or wipes, such that the used diaper and wipes may be discarded together with changing article 100. In embodiments, changing article 100 may be referred to as a disposable changing pad, a diaper changing pad, a baby changing pad, disposable pad, a changing pad, or a "chuck," among other similar terms without intent to limit.

As shown, body 102 of changing article 100 may include a central portion 118 and a perimeter edge 120 surrounding the central portion 118. Central portion 118 may include or be defined by an absorbent pad 124. For example, absorbent pad 124 may include a plurality of liners (e.g., two liners, three liners, more than three liners) to absorb liquids and keep moisture from the skin of an infant or toddler (or another person). In embodiments, perimeter edge 120 may be sealed to limit leakage. Body 102 may have many size and shape configurations. For example, body 102 may be sized such that changing article 100 has a 36"×26" configuration, although other configurations are contemplated. As shown, body 102 may have a rectangular shape, although other configurations are contemplated, including square, polygonal, oval, circular, etc.

With continued reference to FIG. 1, the storage pocket(s) 106 may be positioned at the perimeter edge 120 and include an opening 130 directed toward the central portion 118 of the body 102 (e.g., towards the center of changing article 100). For example, a plurality of storage pockets 106 may be positioned around the central portion 118. As shown, body 102 defines at least one corner 134, such as first, second, third, and fourth corners 134A, 134B, 134C, 134D. In such examples, each storage pocket 106 may be positioned at a respective corner 134 of body 102. For instance, a first storage pocket 106A may be positioned at first corner 134A, and a second storage pocket 106B may be positioned at second corner 134B. In embodiments, first and second corners 134A, 134B may be adjacent such that first and second storage pockets 106A, 106B are positioned adjacent to each other, although other configurations are contemplated, including first and second storage pockets 106A, 106B positioned diagonally across from each other, or the like. In embodiments, storage pocket(s) 106 may extend diagonally across its respective corner 134.

FIG. 2 illustrates a fragmentary view of changing article 100 and showing a corner 134 (e.g., first corner 134A) of changing article 100, in accordance with an embodiment of the disclosure. Referring to FIG. 2, each storage pocket 106 may define a cavity 202 with sufficient volume to store one or more changing accessories 110. For example, each storage pocket 106 may be flexible, deformable, and/or expandable to fit one or more changing accessories 110 at least partially therein. As shown, at least a portion of absorbent pad 124 may be positioned within a storage pocket 106 (e.g., each storage pocket 106), such as to absorb liquids within the storage pocket 106. Opening 130 may be directed toward the center of changing article 100, such as toward absorbent pad 124, for convenient placement of items therein.

Figures 3, 4:
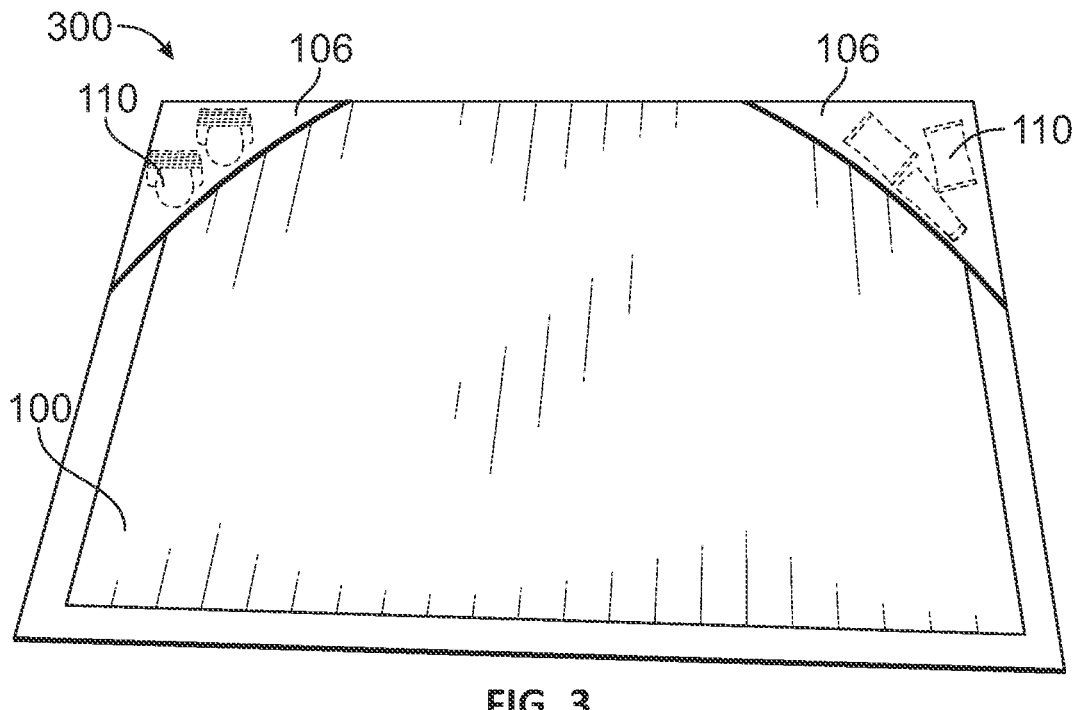
FIG. 3 illustrates a perspective view of a changing system utilizing the disposable changing article of FIG. 1, in accordance with an embodiment of the disclosure.
FIG. 4 illustrates a perspective view of another disposable changing article, in accordance with an embodiment of the disclosure.

FIG. 3 illustrates a perspective view of a changing system 300, in accordance with an embodiment of the disclosure. Referring to FIG. 3, changing system 300 includes changing article 100 and at least one changing accessory 110 for positioning within a storage pocket 106 of changing article 100. For example, changing system 300 may include changing article 100 and at least one diaper, wipes, ointment, or lotion for positioning within a storage pocket 106 of changing article 100.

In some embodiments, changing system 300 may be provided as a kit. For example, a first kit may include changing article 100 and a diaper positioned, or for user positioning, within a storage pocket 106 of changing article 100. Similarly, a second kit may include changing article 100 and one or more wipes (e.g., a package of wipes) positioned, or for user positioning, within a storage pocket 106 of changing article 100. A third kit may be a combination of first kit and second kit. For instance, the third kit may include changing article 100, a diaper positioned or for user positioning within first storage pocket 106A, and one or more wipes (e.g., a package of wipes) positioned or for user positioning within second storage pocket 106B. Other kits may include other changing accessories 110 and/or combinations of changing accessories 110. In some embodiments, different kits may be provided for different diaper sizes.

In this manner, changing system 300 may provide a convenient system for a parent, babysitter, or other caregiver to change the diaper of an infant, baby, or adult. For example, changing system 300 may provide some or all essentials of diaper changing in a convenient disposable package. Such systems may be particularly beneficial for travel or other outings outside the home or care facility.

FIG. 4 illustrates a perspective view of another disposable changing article 400, in accordance with an embodiment of the disclosure. Except as otherwise noted below, changing article 400 of FIG. 4 may be similar to changing article 100 described above. For example, changing article 400 may include body 102 having absorbent pad 124 and perimeter edge 120 surrounding the absorbent pad 124, and at least one storage pocket 106 each positioned at the perimeter edge 120 and including opening 130 directed toward the absorbent pad 124.

Referring to FIG. 4, changing article 400 includes a third storage pocket 106C and a fourth storage pocket 106D. As shown, third storage pocket 106C is positioned at third corner 134C of body 102, and fourth storage pocket 106D is positioned at fourth corner 134D of body 102. Although changing article 100 of FIG. 1 is illustrated as having two storage pockets 106 and changing article 400 of FIG. 4 is illustrated as having four storage pockets 106, changing article 100 and/or changing article 400 may include any number of storage pockets 106, such as a single storage pocket 106, two storage pockets 106, three storage pockets 106, four storage pockets 106, or more than four storage pockets 106 to provide a desired storage configuration for changing article 100/400.

Figure 5:
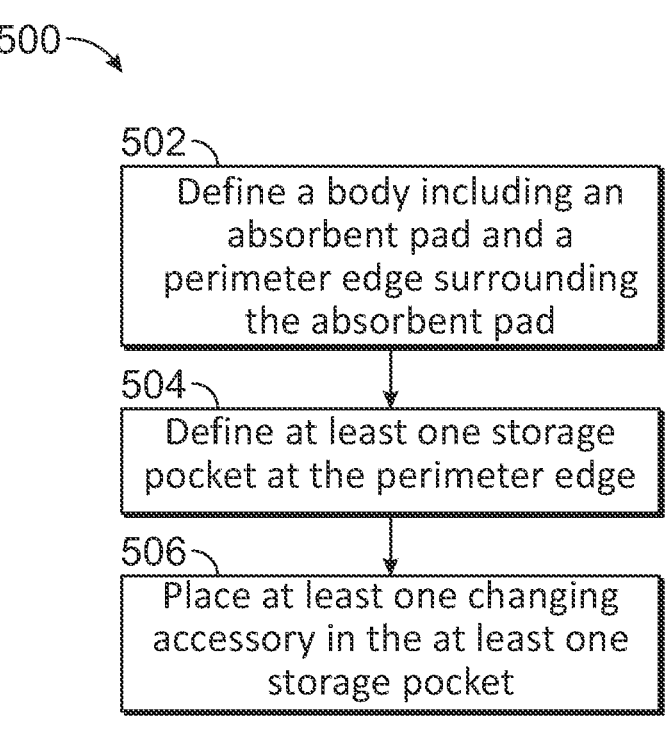
FIG. 5 illustrates a process of manufacturing a disposable changing article, in accordance with an embodiment of the disclosure.

FIG. 5 illustrates a process 500 of manufacturing a disposable changing article, such as changing article 100 and/or changing article 400, in accordance with an embodiment of the disclosure. Process 500 is illustrated as a set of operations or steps and is described with reference to FIGS. 1-4, although process 500 may be applied to other embodiments not illustrated in FIGS. 1-4. One or more steps that are not expressly illustrated in FIG. 5 may be included before, after, in between, or as part of the illustrated steps.

In block 502, process 500 includes defining body 102 including absorbent pad 124 and perimeter edge 120 surrounding absorbent pad 124. Absorbent pad 124 may be provided with multiple liners to absorb liquids. In embodiments, body 102 may be defined to have a quadrilateral shape (e.g., rectangle, square, etc.) with multiple corners 134, although other configurations are contemplated.

In block 504, process 500 includes defining at least one storage pocket 106 at perimeter edge 120, each storage pocket 106 including opening 130 directed toward absorbent pad 124 of body 102. In embodiments, block 504 may include defining a plurality of storage pockets 106 at respective corners 134 of body 102, such as similar to the embodiments illustrated in FIGS. 2 and 4, although other configurations are contemplated as detailed above. In embodiments, the storage pockets 106 may be sized to receive one or more diapers, wipes, ointment, or lotion. In embodiments, at least a portion of absorbent pad 124 may be positioned within at least one storage pocket 106.

In block 506, process 500 may include placing one or more changing accessories 110 in at least one storage pocket 106. For example, one or more changing accessories 110 may be placed in one or more storage pockets 106 and provided as a kit (e.g., changing system 300) for purchase and/or use by a caregiver, as described above.

All relative and directional references (including up, down, upper, lower, top, bottom, side, front, rear, and so forth) are given by way of example to aid the reader's understanding of the examples described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

The present disclosure teaches by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A disposable diaper changing article consisting of:
a body having a square or rectangular shape defined by first, second, third, and fourth corners, the body comprising a perimeter edge consisting of a first linear edge extending from the first corner to the second corner, a second linear edge extending from the second corner to the third corner, a third linear edge extending from the third corner to the fourth corner, and a fourth linear edge extending from the first corner to the fourth corner;
first, second, third, and fourth storage pockets at the first, second, third, and fourth corners, respectively, each storage pocket positioned at the perimeter edge and comprising an opening directed inwardly toward a central portion of the body;
an absorbent pad positioned at least partially within each of the first, second, third, and fourth storage pockets; and
one or more changing accessories, separate from the absorbent pad, positioned within at least one storage pocket of the first, second, third, and fourth storage pockets, as provided in a kit.

2. The disposable changing article of claim 1, wherein an entire periphery of the disposable changing article comprises no more than four corners.

3. The disposable changing article of claim 1, wherein the first, second, third, and fourth storage pockets are positioned at adjacent corners of the central portion.

4. The disposable changing article of claim 1, wherein each storage pocket extends diagonally across the respective corner.

5. The disposable changing article of claim 1, wherein the first, second, third, and fourth storage pockets are positioned around the central portion.

6. The disposable changing article of claim 1, wherein the absorbent pad comprising a plurality of liners.

7. The disposable changing article of claim 6, wherein at least a portion of each liner of the plurality of liners is positioned within the first, second, third, and fourth storage pockets.

8. The disposable changing article of claim 1, further comprising:
a second changing accessory positioned within another storage pocket of the first, second, third, and fourth storage pockets, as provided in the kit.

9. The disposable changing article of claim 8, wherein the changing accessory comprises a first one of one or more diapers, wipes, ointment, or lotion, and wherein the second changing accessory comprises a second one of the one or more diapers, wipes, ointment, or lotion.

10. A system provided as a kit, the system comprising:
a disposable diaper changing article consisting of:
a body having a square or rectangular shape defined by first, second, third, and fourth corners, the body comprising a perimeter edge consisting of a first linear edge extending from the first corner to the second corner, a second linear edge extending from the second corner to the third corner, a third linear edge extending from the third corner to the fourth corner, and a fourth linear edge extending from the first corner to the fourth corner,
an absorbent pad comprising a plurality of liners, wherein at least a portion of the absorbent pad is positioned within at least one storage pocket of the first, second, third, and fourth storage pockets, and
first, second, third, and fourth storage pockets at the first, second, third, and fourth corners, respectively, of the body, each storage pocket positioned at the perimeter edge and comprising an opening directed toward the absorbent pad; and
a changing accessory, separate from the absorbent pad, positioned within one of the first, second, third, or fourth storage pocket for convenient location of the changing accessory on the body.

11. The system of claim 10, wherein an entire periphery of the disposable changing article consists of four corners.

12. The system of claim 10, further comprising:
a second changing accessory positioned within another one of the first, second, third, or fourth storage pocket for convenient location of the second changing accessory on the body,
wherein the changing accessory and the second changing accessory are positioned at adjacent corners of the body.

13. The system of claim 10, wherein at least one storage pocket of the first, second, third, and fourth storage pockets extends diagonally across the respective corner.

14. The system of claim 10, wherein the first, second, third, and fourth storage pockets are positioned around the body at the perimeter edge.

15. The system of claim 10, wherein the changing accessory comprises one or more diapers, wipes, ointment, or lotion positioned within at least one storage pocket of the first, second, third, and fourth storage pockets.

16. A method of manufacturing a disposable diaper changing article, the method comprising:

defining a body having a square or rectangular shape defined by first, second, third, and fourth corners, the body comprising a perimeter edge consisting of a first linear edge extending from the first corner to the second corner, a second linear edge extending from the second corner to the third corner, a third linear edge extending from the third corner to the fourth corner, and a fourth linear edge extending from the first corner to the fourth corner;

positioning at least a portion of an absorbent pad within at least one storage pocket of the first, second, third, and fourth storage pockets, the absorbent pad comprising a plurality of liners;

defining first, second, third, and fourth storage pockets at the first, second, third, and fourth corners, respectively, along the perimeter edge, each storage pocket comprising an opening directed toward the absorbent pad of the body, and positioning, as provided in a kit, a changing accessory within a storage pocket of the first, second, third, and fourth storage pockets, the changing accessory separate from the absorbent pad.

17. The method of claim 16, wherein the defining the first, second, third, and fourth storage pockets comprises defining a storage pocket diagonally at each corner of the body.

18. The method of claim 16, wherein each storage pocket is sized to receive one or more diapers, wipes, ointment, or lotion.

* * * * *